US012729228B2

(12) United States Patent
Lee et al.

(10) Patent No.: US 12,729,228 B2
(45) Date of Patent: Sep. 8, 2026

(54) TRANSFORMING GROWTH FACTOR BETA-RESISTANT NATURAL KILLER CELLS

(71) Applicant: RESEARCH INSTITUTE AT NATIONWIDE CHILDREN'S HOSPITAL, Columbus, OH (US)

(72) Inventors: Dean Anthony Lee, Canal Winchester, OH (US); Jennifer Ann Foltz-Stringfellow, St. Louis, MO (US); Jena Edwards-Moseman, Columbus, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 1354 days.

(21) Appl. No.: 16/966,367

(22) PCT Filed: Jan. 29, 2019

(86) PCT No.: PCT/US2019/015617
§ 371 (c)(1),
(2) Date: Jul. 30, 2020

(87) PCT Pub. No.: WO2019/152387
PCT Pub. Date: Aug. 8, 2019

(65) Prior Publication Data

US 2020/0368281 A1 Nov. 26, 2020

Related U.S. Application Data

(60) Provisional application No. 62/623,682, filed on Jan. 30, 2018.

(51) Int. Cl.

| | |
|---|---|
| ***A61K 40/15*** | (2025.01) |
| ***A61K 40/42*** | (2025.01) |
| ***C07K 14/475*** | (2006.01) |
| ***C12N 5/0783*** | (2010.01) |
| *A61K 38/00* | (2006.01) |

(52) U.S. Cl.
CPC ............ *C07K 14/475* (2013.01); *A61K 40/15* (2025.01); *A61K 40/4229* (2025.01); *C12N 5/0646* (2013.01); *A61K 38/00* (2013.01); *A61K 2239/48* (2023.05); *A61K 2239/55* (2023.05)

(58) Field of Classification Search
None
See application file for complete search history.

(56) References Cited

U.S. PATENT DOCUMENTS

| | | | |
|---|---|---|---|
| 2010/0303779 A1 | 12/2010 | Marie | |
| 2017/0037371 A1* | 2/2017 | Zhang .................. | C12N 5/0637 |
| 2017/0056448 A1 | 3/2017 | Glick et al. | |
| 2017/0333479 A1 | 11/2017 | Copik | |

FOREIGN PATENT DOCUMENTS

| | | |
|---|---|---|
| JP | 2017532353 A | 11/2017 |
| WO | 2017048809 A1 | 3/2017 |

OTHER PUBLICATIONS

Butler et al., Immunology Reviews, vol. 257, Issue 1 191-209 (2014), (Year: 2014).*
Otegbeye et al., Blood (2016) 128 (22): 2160, 4 pages, 703 Adoptive Immunotherapy: POSTER I, Dec. 2, 2016 (Year: 2016).*
Laouar Yasmina et al ,Transforming growth factor-beta controls T helper type 1 cell development through regulation of natural killer cell interferon-gamma, Nature Immulogy, Nature Publishing Group US, New York, vol. 6, No. 6, Apr. 24, 2005 (Apr. 24, 2005), pp. 600-607.
Marie Julien C et al: Cellular mechanisms of fatal early-onset autoimmunity in mice with the T cell-specific targeting of transforming growth factor-beta receptor, Immunity, Cell Press, vol. 25, No. 3, Sep. 1, 2006 (Sep. 1, 2006), pp. 441-454.
Jianhua Yu et al: Pro- and Antiinflammatory Cytokine Signaling: Reciprocal Antagonism Regulates Interferon-gamma Production by Human Natural Killer Cells, Immunity, vol. 24, No. 5, May 1, 2006 (May 1, 2006), pp. 575-590.
Silver Jonathan S et al. NK cells join the plasticity party, Nature immunology, Aug. 22, 2017 (Aug. 22, 2017), pp. 959-960.
D. Sarhan et al: Adaptive NK Cells with Low TIGIT Expression Are Inherently Resistant to Myeloid-Derived Suppressor Cells, Cancer Research, vol. 76, No. 19, Aug. 8, 2016 (Aug. 8, 2016), pp. 5696-5706.
Jennifer Foltz et al: TGF[beta] Imprinting During Activation Promotes Natural Killer Cell Cytokine Hypersecretion, Cancers, vol. 10, No. 423, Nov. 5, 2018 (Nov. 5, 2018), pp. 1-19.
Search Report issued in EP Application No. 19747119; dated Oct. 27, 2021; 16 pages.
Li et al. Transforming Growth Factor-B Regulation of Immune Responses, Annu, Rev. Immunol., vol. 24, pp. 99-146, 2005.
English translation of Japanese Office Action issued in JP2020-562093, mailed Jul. 25, 2023.
English translation of Russian Office Action issued in RU2020127722/10, mailed Jul. 18, 2023.
Alizadeh et al. "Induction of anti-glioma natural killer cell response following multiple low-dose intracerebral CpG therapy." Clinical Cancer Research 16.13 (2010): 3399-3408.
Bellone, et al. "Regulation of NK cell functions by TGF-beta 1." The Journal of Immunology 155.3 (1995): 1066-1073.

(Continued)

*Primary Examiner* — Evelyn Y Pyla
(74) *Attorney, Agent, or Firm* — Meunier Carlin & Curfman LLC

(57) ABSTRACT

An NK cell with low SMAD3 expression and altered gene expression profile resulting in high cytokine expression and TGF-β superfamily resistance is described, refered to herein as TGF-β superfamily-imprinted Natural Killer Cells (TGFβi NK cells). A method of treating cancer or infection in a subject in need thereof is described. The method includes administering a therapeutically effective number of TGFβi NK cells to the subject. A method of producing TGFβi NK cells is described by in vitro activation of natural killer cells in the presence of a TGF-β superfamily cytokine.

15 Claims, 11 Drawing Sheets

(56) References Cited

OTHER PUBLICATIONS

Figure 1:
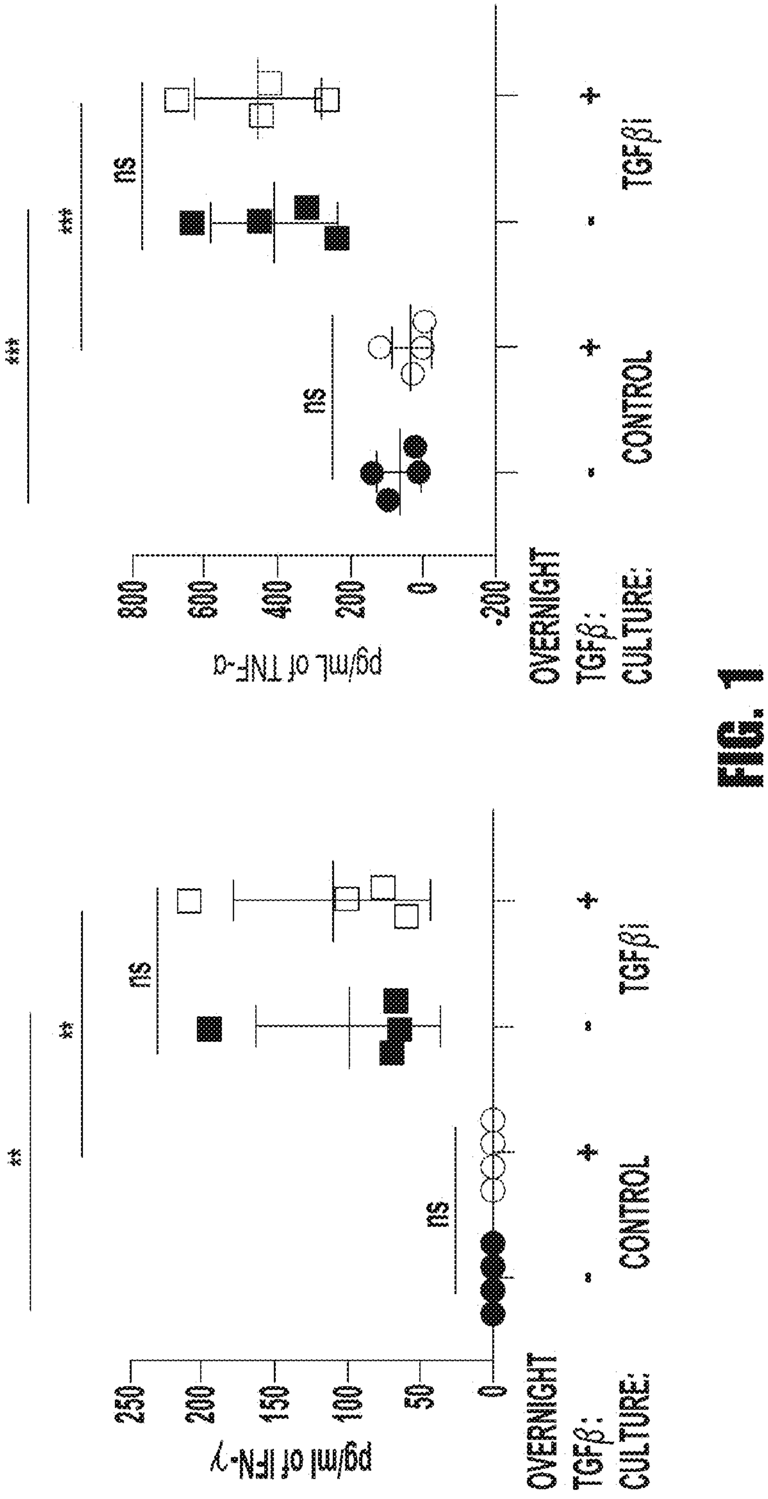

Berg et al. "Clinical-grade ex vivo-expanded human natural killer cells up-regulate activating receptors and death receptor ligands and have enhanced cytolytic activity against tumor cells." Cytotherapy 11.3 (2009): 341-355.
Bollard et al. "Adapting a transforming growth factor β—related tumor protection strategy to enhance antitumor immunity." Blood, The Journal of the American Society of Hematology 99.9 (2002): 3179-3187.
Castriconi et al. "Neuroblastoma-derived TGF-β1 modulates the chemokine receptor repertoire of human resting NK cells." The Journal of Immunology 190.10 (2013): 5321-5328.
Childs et al. "Bringing natural killer cells to the clinic: ex vivo manipulation." Hematology 2013, the American Society of Hematology Education Program Book 2013.1 (2013): 234-246.
Denman et al. "Membrane-bound IL-21 promotes sustained ex vivo proliferation of human natural killer cells." PloS one 7.1 (2012): e30264.
Derynck et al. "Transcriptional activators of TGF-β responses: Smads." Cell 95.6 (1998): 737-740.
Kawano et al. "Anti-TGF-β antibody combined with dendritic cells produce antitumor effects in osteosarcoma." Clinical Orthopaedics and Related Research® 470.8 (2012): 2288-2294.
Keskin et al. "TGFβ promotes conversion of CD16+ peripheral blood NK cells into CD16—Nk cells with similarities to decidual NK cells." Proceedings of the National Academy of Sciences 104.9 (2007): 3378-3383.
Lamora et al., "Overexpression of smad7 blocks primary tumor growth and lung metastasis development in osteosarcoma." Clinical Cancer Research 20.19 (2014): 5097-5112.
Li et al. "Bifacial effects of engineering tumour cell-derived exosomes on human natural killer cells." Experimental cell research 363.2 (2018): 141-150.
Li et al. "Transforming growth factor-β controls development, homeostasis, and tolerance of T cells by regulatory T cell-dependent and-independent mechanisms." Immunity 25.3 (2006): 455-471.
Loftus et al. "Activation of human natural killer cells by graphene oxide-templated antibody nanoclusters." Nano letters 18.5 (2018): 3282-3289.
Oida, Takatoku, and Howard L. Weiner. "Depletion of TGF-β from fetal bovine serum." Journal of immunological methods 362.1-2 (2010): 195-198.
Somanchi et al. "Expansion, purification, and functional assessment of human peripheral blood NK cells." JoVE (Journal of Visualized Experiments) 48 (2011): e2540.
Tang et al. "Smad3 promotes cancer progression by inhibiting E4BP4-mediated NK cell development." Nature communications 8.1 (2017): 1-15.
Viel et al. "TGF-β inhibits the activation and functions of NK cells by repressing the mTOR pathway." Science signaling 9.415 (2016): ra19-ra19.
Wallace et al. "Transforming growth factor-β receptor blockade augments the effectiveness of adoptive T-cell therapy of established solid cancers." Clinical Cancer Research 14.12 (2008): 3966-3974.
Wilson et al. "Human tumour immune evasion via TGF-β blocks NK cell activation but not survival allowing therapeutic restoration of anti-tumour activity." PloS one 6.9 (2011): e22842.
Wrzesinski et al. "Transforming growth factor-β and the immune response: implications for anticancer therapy." Clinical cancer research 13.18 (2007): 5262-5270.
Xu et al. "Transforming growth factor-beta polymorphisms and serum level in the development of osteosarcoma." DNA and Cell Biology 33.11 (2014): 802-806.
Hayashi et al.: "TGFβ down-regulates IFN-gamma production in IL-18 treated NK cell line LNK5E6", Biochemical and Biophysical Research Communications, vol. 300, No. 4, Jan. 24, 2003 (Jan. 24, 2003), pp. 980-985.
Yu et al.: "Pro-and antiinflammatory cytokine signaling: reciprocal antagonism regulates interferon-gamma production by human natural killer cells", Immunity, vol. 24, No. 5, May 1, 2006 (May 1, 2006), pp. 575-590.
International Search Report and Written Opinion issued for International Application No. PCT/US2019/015617 mailed May 31, 2019.
International Preliminary Report on Patentability issued for International Application No. PCT/US2019/015617 mailed Aug. 13, 2020.
Wu Y. et al., Developmental and Functional Control of Natural Killer Cells by Cytokines. Front Immunol, Aug. 4, 2017, vol. 8, No. 930, pp. 1-18.
Fujisaki et al., Expansion of Highly Cytotoxic Human Natural Killer Cells for Cancer Cell Therapy, Cancer Res 2009; 69: (9). May 1, 2009, pp. 4010-4017.
Svirshchevskaya et al., Activation of NK Cells in Mixed Cultures of Wharton's Jelly Mesenchymal Stromal Cells and Peripheral Blood Lymphocytes, Translated from Byulleten' Eksperimental'noi Biologii i Meditsiny, vol. 164, No. 9, pp. 320-325, Sep. 2017.
Szmania S., et al., "Ex Vivo Expanded Natural Killer Cells Demonstrate Robust Proliferation In Vivo In High-Risk Relapsed Multiple Myeloma Patients", Journal of Immunother, Jan. 2015, vol. 38, No. 1, 26 pages.

* cited by examiner

TRANSFORMING GROWTH FACTOR BETA-RESISTANT NATURAL KILLER CELLS

CROSS-REFERENCE TO RELATED APPLICATIONS

This application is a national stage application filed under 35 U.S.C. § 371 of PCT/US2019/015617 filed Jan. 29, 2019, which claims priority to U.S. Provisional Patent Application No. 62/623,682, filed on Jan. 30, 2018, which are hereby incorporated by reference in their entireties.

BACKGROUND

Clinicians have sought to use natural killer (NK) cells for adoptive transfer because of their ability to recognize and kill tumor cells without requiring any particular tumor cell marker. Alizadeh et al., Clin Cancer Res, 16(13): 3399-3408 (2010). However development of NK cell adoptive transfer procedures has been impeded by the limited supply of viable cells. NK cells represent only a small fraction of the cells in blood and isolation from a typical blood draw does not yield many cells. Furthermore, NK cells must be purified away from contaminating PBMCs such as T and B cells by CD3 and CD19 depletion, respectively. Childs et al., American Society of Hematology (ASH) Education Book, vol. 2013 no. 1 234-246 (2013). This is a necessary step for allogenic transplantation where the presence of T and B cells increases risk of graft versus host disease (GVHD) but further reduces the NK cell yield.

NK cells expand poorly in vitro compared to others kinds of cells due mainly to early senescence. Using even the most effective methods, NK cells are susceptible to telomere shortening and senescence after only a few passages. Demnan el al., PLoS ONE 7(1): e30264 (2012), The most effective method for increasing NK cell viability and proliferation in vitro is co-culturing with feeder cells. Commonly used feeder cells for NK cell expansion include irradiated peripheral blood mononuclear cells (PBMCs), Epstein-Barr virus-transformed lymphoblastoid cell lines (EBV-LCL), gene-modified K562 cells constitutively expressing IL-15 or 21, and other irradiated tumor cell lines. Berg et al., Cytotherapy, 11(3):341-55 (2009). Co-culturing with feeder cells significantly increases NK cell viability and proliferation with population increases between 1,000 and 50,000 times.

Immune therapy holds great promise for improving the outcome of cancers such as osteosarcoma (OS), where survival has not improved over the last 30 years. OS, including chemotherapy-resistant OS, is readily killed in vitro by both autologous and allogeneic activated NK cells. However, the tumor microenvironment in OS, and other solid tumors, has elevated levels of the highly immunosuppressive cytokine, transforming growth factor-beta (TGF-β). Lamora et al., Clin Cancer Res 20: 5097-5112 (2014); Xu et al., DNA Cell Biol, 33: 802-806 (2014). The addition of a blocking antibody to TGF-β improved the efficacy of a dendritic cell vaccine in OS (Kawano et al., Clin Orthop Relat Res., 470: 2288-2294 (2012)), providing proof of principle that TGF-β is actively inhibiting immune therapies in OS.

TGF-β's suppression of NK cell function is multi-faceted. TGF-β modulates the development of NK cells and subsequently negatively affects their function upon reaching maturation. TGF-β promotes an immature NK cell lineage, by preventing the progression of NK cells into CD16+NK cells. TGF-β can also induce formerly CD16+NK cells to become CD16-. Keskin et al., Proc Natl Acad Sci USA, 104: 3378-3383 (2007). In addition, mice expressing a dominant negative TGFβR on NK cells have increased numbers of mature NK cells compared to wild-type mice. Viel et al., Science signaling 9: ra19 (2016).

In mature NK cells, TGF-β inhibits anti-tumor activity through multiple mechanisms. TGF-β decreases IL-2 and IL-15 induced NK cell proliferation (Wilson et al., PloS one 6: e22842 (2011)), and IL-15 induced mTOR activation. Viel et al., Sci Signal., 16;9(415):ra19 (2016). TGF-β also inhibits IFNγ secretion, which is important for stimulating the adaptive immune system and can sensitive tumors to NK cell lysis. TGF-β inhibits IFNγ both directly and indirectly. SMAD3 directly binds to the IFNγ promoter and can also inhibit IFNγ indirectly by decreasing expression of the IFNγ-promoting transcription factors, T-bet and E4BP4. Tang et al., Nat Commun, 8: 14677 (2017). However, TGF-β mediated inhibition of IFNγ secretion can be partially alleviated by pre-incubation of NK cells with IL-12, IL-15, or IL-18. Yu et al., Immunity, 24: 575-590 (2006). Furthermore, TGF-β also inhibits INFα and GM-CSF secretion and modulates chemokine receptor expression to promote the retention of NK cells within the bone marrow. Castriconi et al., J Immunol, 190: 5321-5328 (2013).

Specifically, TGF-β mediates its' inhibition of NK cell cytotoxicity by decreasing Granzyme and Perforin secretion, and expression of the following activating receptors: NKG2D, NKp30, KIRs, DNAM-1, NKp44, TRAIL, and CD16. This inhibits NK cell recognition of malignant cells expressing their cognate ligands.

There have been several approaches towards generating NK and T-cells resistant to TGF-β. These include dominant negative TGFβRII expressing cells and combination therapies using TGF-β small molecule inhibitors with immune-based therapies. Importantly, all of these methods have demonstrated increased in vitro and in vivo efficacy of NK and T-cell therapies. Wallace et al., Clin Cancer Res., 14(12):3966-74 (2008); Bollard, C., Blood, 99: 3179-3187 (2002). However, broad spectrum inhibition of TGF-β has potential for adverse side effects; since TGF-β signaling is context dependent and can have both tumor-promoting and tumor-suppressive effects. For example, the inhibition of TGF-β in murine models increased the number of circulating tumor cells (Wrzesinski et al., Clin Cancer Res., 13: 5262-5270 (2007)), and broad spectrum inhibition of TGF-β causes profound autoimmune disease. Li et al., Immunity 25: 455-471 (2006). Therefore, inhibition of TGF-β should be done only with caution and after determining the tumor's responsiveness to TGF-β. Thus, non-systemic methods of generating innate TGF-β resistance are a promising alternative to avoid the adverse effects that systemic TGF-β inhibition may have.

SUMMARY

Many types of cancer diminish NK cell killing by the release of TGF-β. The inventors developed a non-genetic method of educating (imprinting) NK cells to be resistant to TGF-β. TGF-β inprinted NK (TGFβi NK) cells were developed by adding TGF-β during stimulation of NK cells with IL-12/15/18. TGFβi NK maintained their cytotoxicity following stimulation better than normal NK cells. Additionally, TGFβi NK cells cultured with TGF-β have increased secretion of IFN-γ, TNF-α, and GM-CSF, which can increase tumor killing and broadly stimulate the adaptive immune response. Increased cytokine secretion persists for more than one month. The resistance to TGF-β persists for at least 1 week in vitro, and is mediated by SMAD3 downregulation.

BRIEF DESCRIPTIONS OF THE DRAWINGS

The present invention may be more readily understood by reference to the following figures, wherein:

FIG. 1 provides graphs showing that NK cell activation with parental (unmodified) K562 in the presence of TGF induces TGFβi NK cells with cytokine hypersecretion in response to tumor targets. NK cells were stimulated weekly with K562 and cultured in the media containing IL-2 (control) or IL-2 and 10 ng/mL TGFβ (TGFβi) for 14 days. Following culture, IFNγ and TNFα secretion was assessed in supernatant after co-culture with MG63 tumor targets. Lines and bars represent Mean±SD. Statistical differences were determined by two-way repeated measures ANOVA with Holm-Sidak's multiple comparisons test for all other graphs. * p≤0.05,  p≤0.01, * p≤0.001, **** p≤0.0001.

Figure 2:
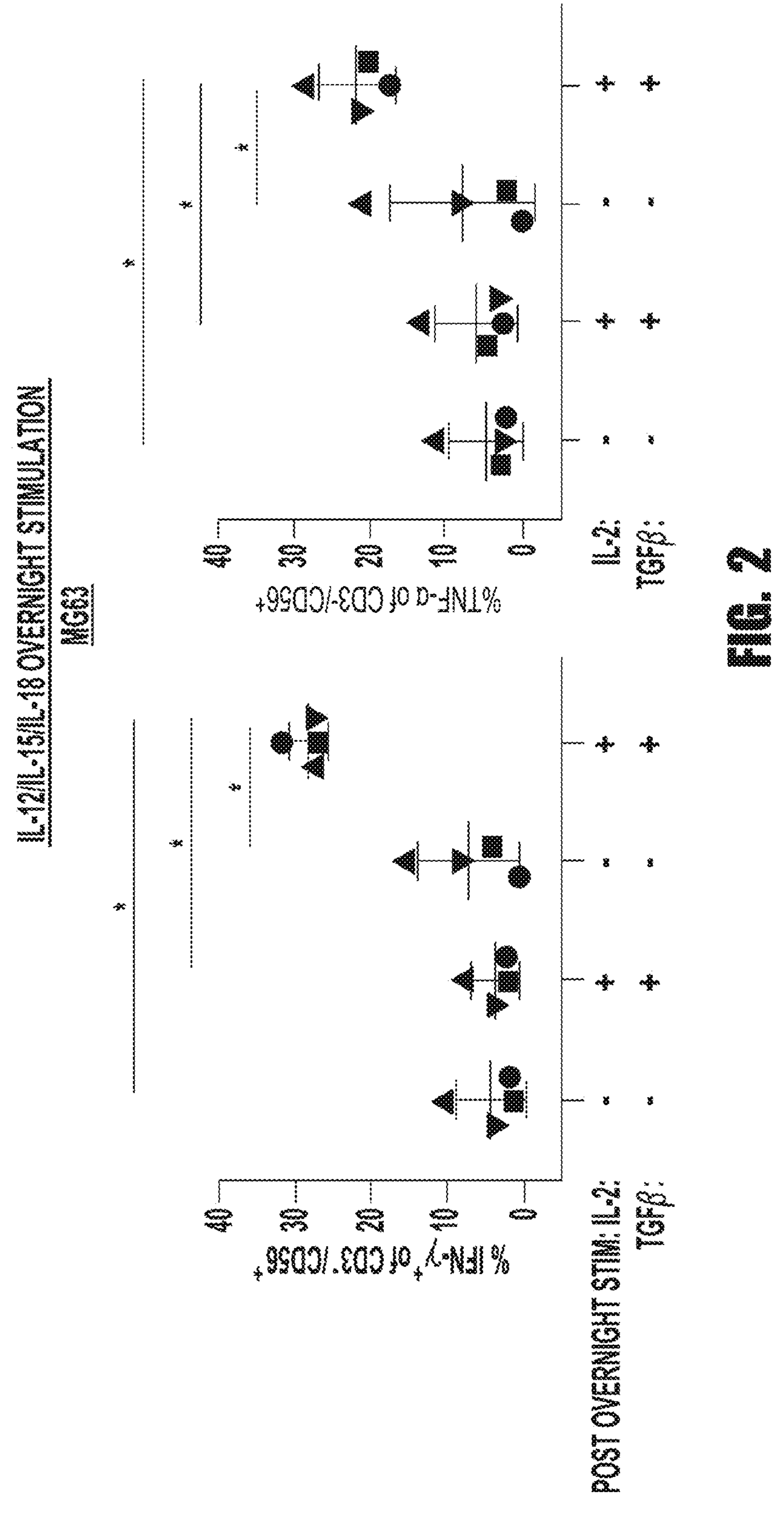

FIG. 2 provides graphs showing that NK cell activation with pro-inflammatory cytokines in the presence of TGFβ induces TGFβi NK cells with cytokine hypersecretion in response to tumor targets. NK cells were activated overnight with IL-12, -15, and -18 (10 ng/mL, 50 ng/mL, and 50 ng/mL respectively) with or without IL-2 and TGF, followed by culture in IL-15 (1 ng/mL) with or without IL-2 and TGFβ. After 7-14 days of culture, anti-tumor IFNγ and TNFα production in response to MG63 was measured by intracellular flow cytometry (n=4). Percent IFNγ+ and TNFα+NK cells normalized to no target. Individual data points (●, ■, ▲) depicted for all. Statistical differences were determined by two-way repeated measures ANOVA with Holm-Sidak's multiple comparisons test for all other graphs. * p≤0.05,  p≤0.01, * p≤0.001, **** p≤0.0001.

Figure 3:
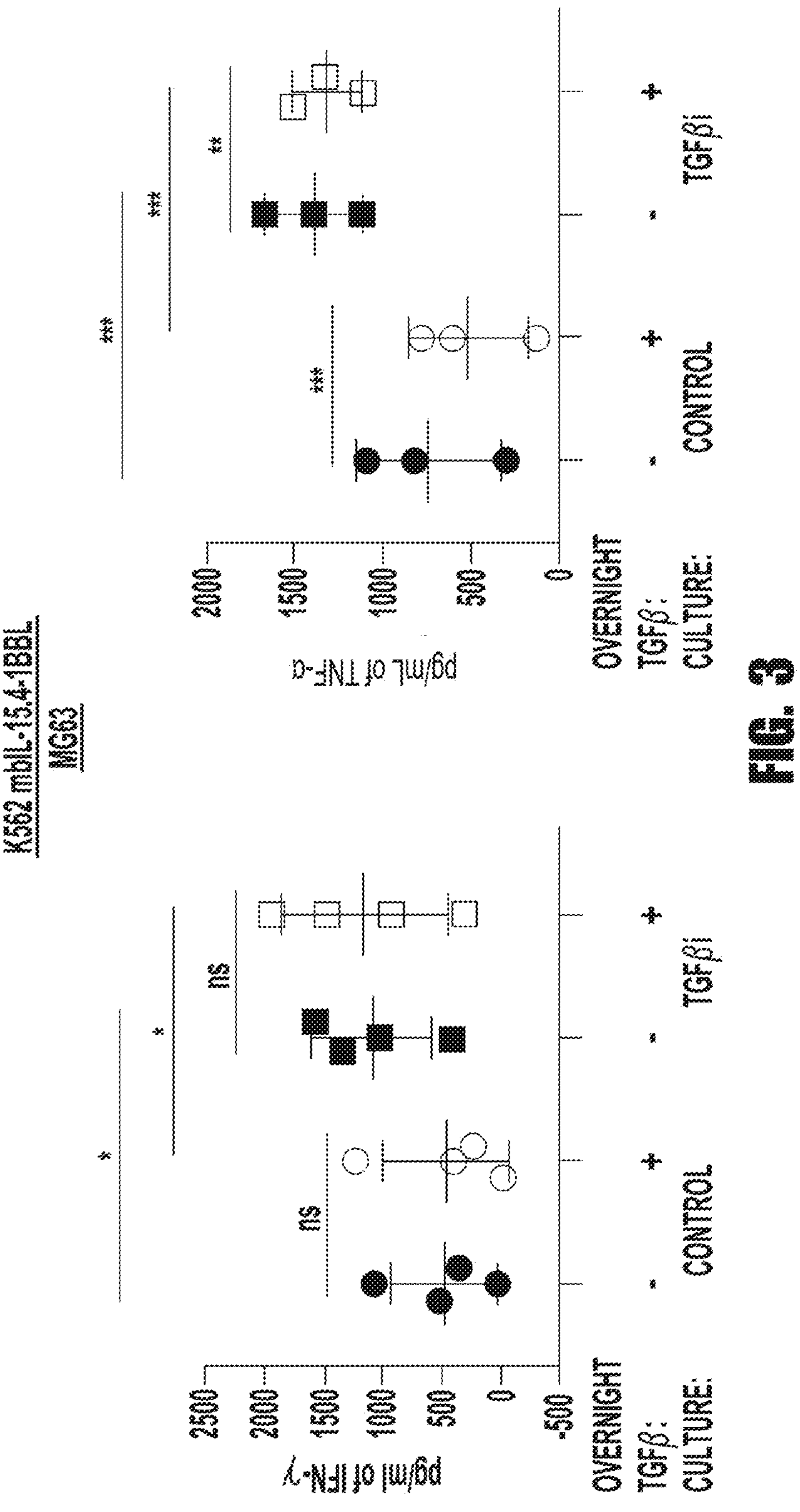

FIG. 3 provides graphs showing that NK cell expansion with K562 mbIL-15 (clone 4) feeder cells in the presence of TGFβ induces TGFβi NK cells with cytokine hypersecretion in response to tumor targets. After 14 days expansion with feeder cells with (TGFβi) or without (control) TGFβ, NK cells were rested overnight in 50 IU/mL IL-2 with or without 10 ng/mL TGFβ. NK cells were then co-cultured with tumor targets in the same media and supernatants were collected to measure cytokine secretion. Control in black, TGFβi in red. Statistical differences were determined by two-way repeated measures ANOVA with Holm-Sidak's multiple comparisons test for all others. * p≤0.05,  p≤0.01, * p≤0.001, **** p≤0.0001.

Figure 4:
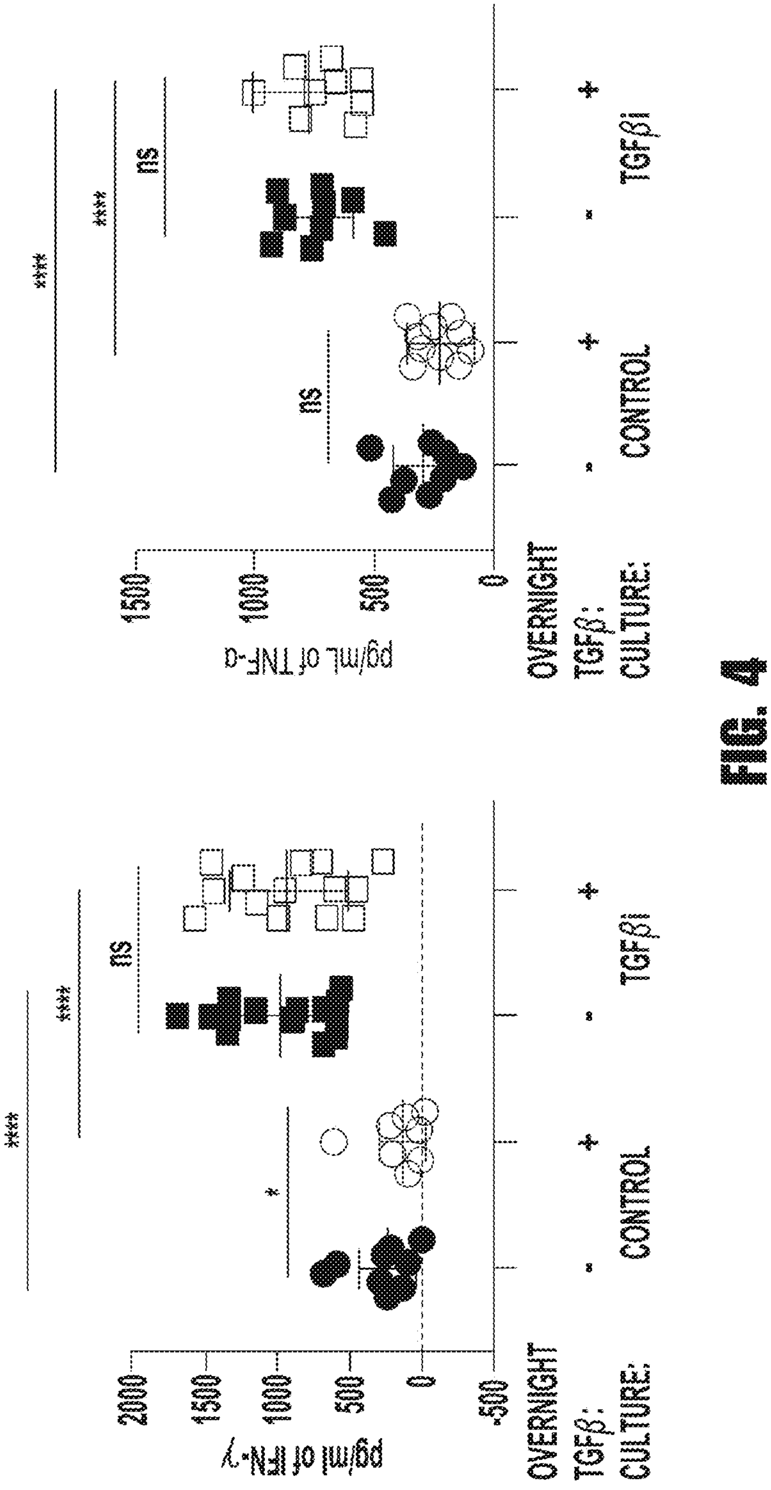

FIG. 4 provides graphs showing that NK cell expansion with K562 mbIL-21 feeder cells in the presence of TGFβ induces TGFβi NK cells with cytokine hypersecretion in response to tumor targets. After 14 days expansion with feeder cells with (TGFβi) or without (control) TGFβ, NK cells were rested overnight in 50 IU/mL IL-2 with or without 10 ng/mL TGFβ, NK cells were then co-cultured with tumor targets in the same media and supernatants were collected to measure cytokine secretion. Control in black, TGFβi in red. Statistical differences were determined by two-way repeated measures ANOVA with Hohn-Sidak's multiple comparisons test for all others. * p≤0.05,  p≤0.01, * p≤0.001, **** p≤0.0001.

Figure 5:
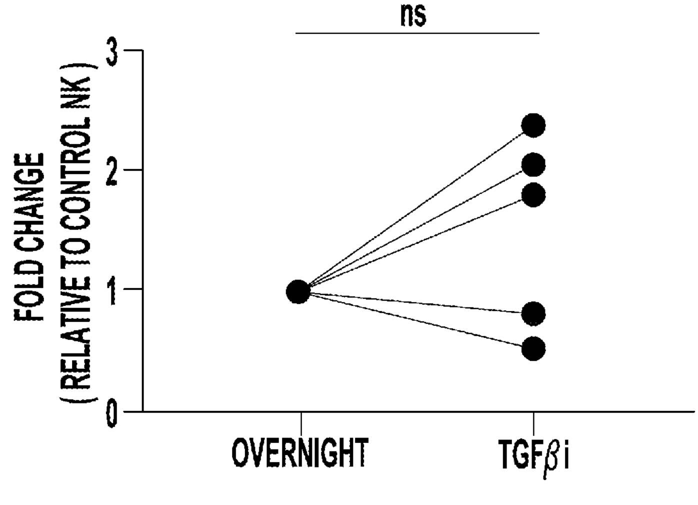

FIG. 5 provides a graph showing that the addition of TGFβ to generate TGFβi NK cells does not reduce proliferative potential in expansion cultures with K562 mbIL-21 (CSTX002) feeder cells. NK cells were expanded for 14 days on feeder cells with (TGFβi) or without (control) TGFβ in paired cultures from 5 donors starting from the same number of cells at Day 0. Total number of viable cells after 14 days is shown, normalized to control NK cells for each paired expansion. Non-significant by Student's paired t test.

Figure 6:
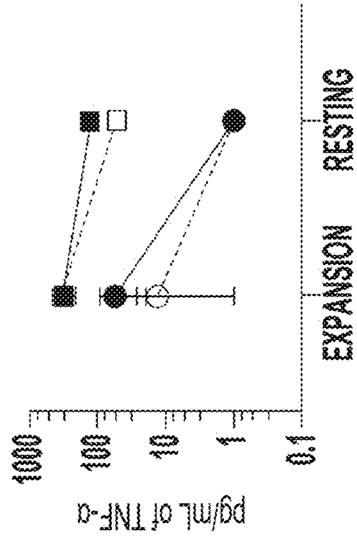
Figure 6:
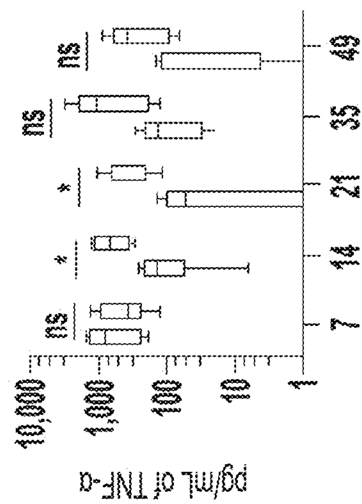
Figure 6:
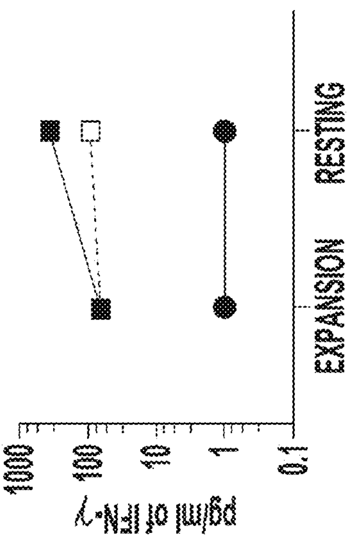
Figure 6:
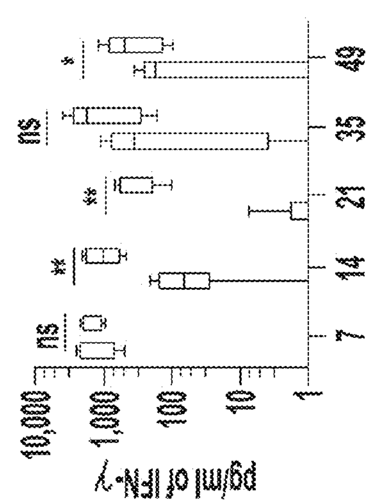

FIG. 6 provides graphs showing that TGFβi NK cells maintain cytokine hypersecretion against tumor cells for weeks. A) TGFβi and control NK cells expanded with parental K562 feeder cells for 14 days (Expansion), or expanded and rested for an additional 7 days (Resting), were co-cultured with MG63 target cells and the supernatant assessed for cytokine secretion. B) In a similar experiment, cytokine secretion against MG63 with K562mbIL-21 expanded control and TGFβ NK cells was assessed at Day 7 and Day 14 of expansion, and again after resting on Day 21, 35, and 47. Median with min to max whiskers depicted. Control in black, TGFβi in red. Statistical differences were determined by paired t-test * p≤0.05,  p≤0.01, * p≤0.001, **** p≤0.0001.

Figure 7:
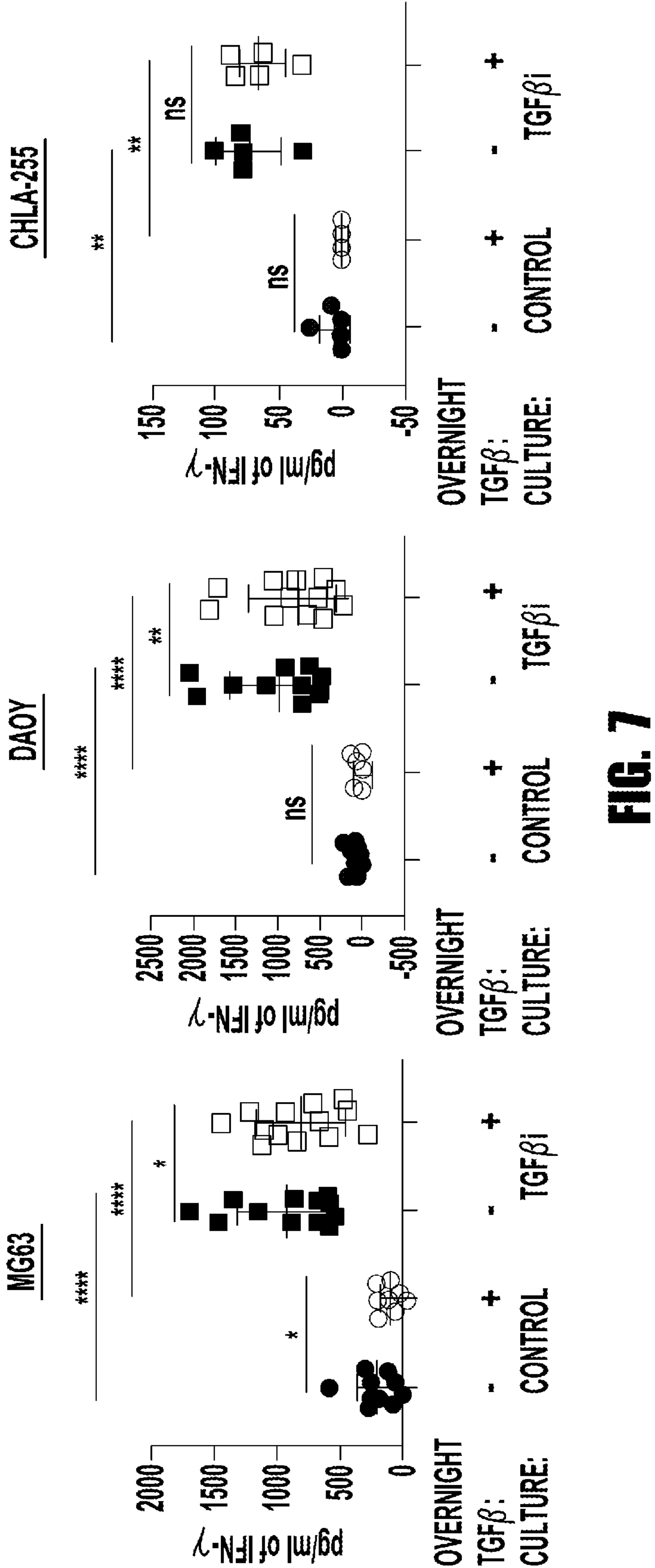

FIG. 7 provides graphs showing that TGFβi NK cells exhibit cytokine hypersecretion against multiple cancer types. After 14 days expansion under control conditions or with TGFβ present to induce TGFβi NK cells, NK cells were rested overnight with or without IL-2 or TGFβ. NK cells were then co-cultured with tumor targets in the same fresh media for 3 hours and supernatants were collected to measure IFNγ cytokine secretion. Individual data points are depicted for MG63, DAOY (medulloblastoma, n=12) and CHLA-255 (neuroblastoma, n=5). Lines and bars represent Mean±SD.

Figure 8:
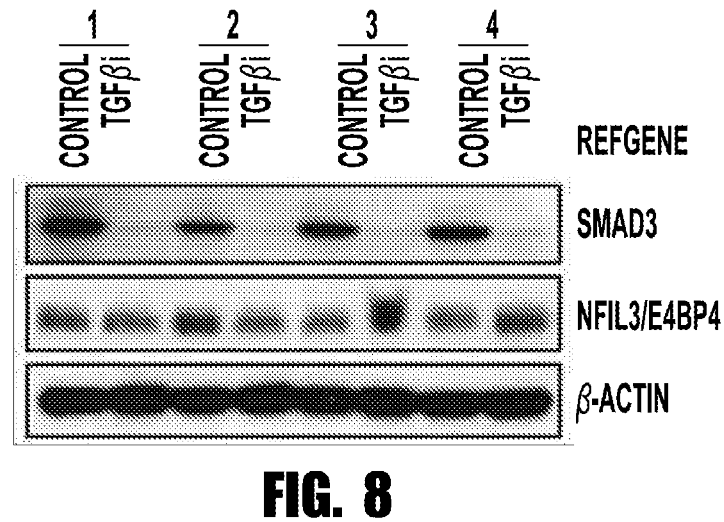
Figure 9:
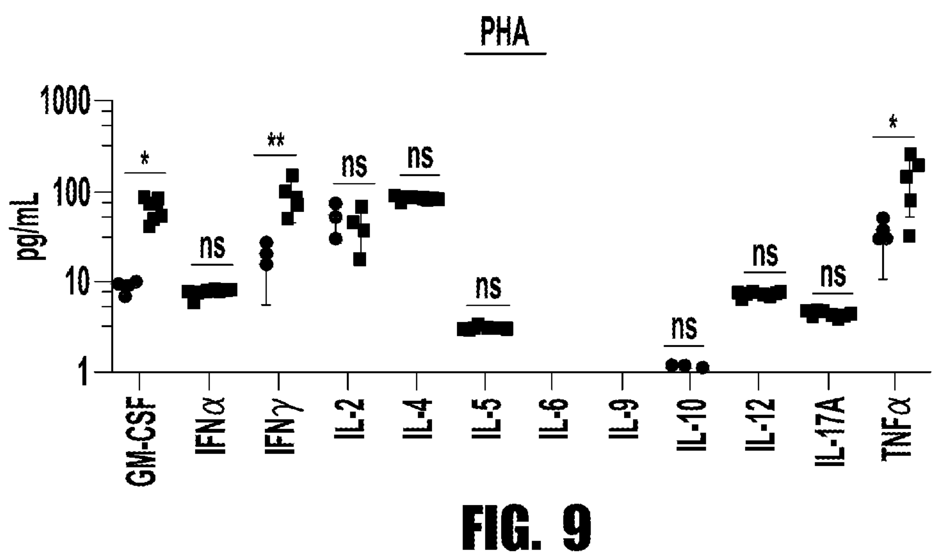

FIG. 8 provides a graph showing that TGFβi NK cells exhibit dramatic downregulation of the TGFβi-signaling protein, SMAD3. After 14 days expansion under control conditions or with TGFβ present to induce TGFβi NK cells, NK cells were assessed for protein expression of SMAD3 and E4BP4 (n=4) by western blot. FIG. 9 provides a graph showing that TGFβi NK cells hypersecrete GM-CSF, TNFα, and IFNγ. Control (●) and TGFβi NK (■) cells were stimulated with 10 μg/mL of PHA at 2×10e6 NK cells/mL for 4 hours and cytokine secretion was measured. Lines and bars represent Mean±SD. Statistical differences were determined by paired t-test.

Figure 10:
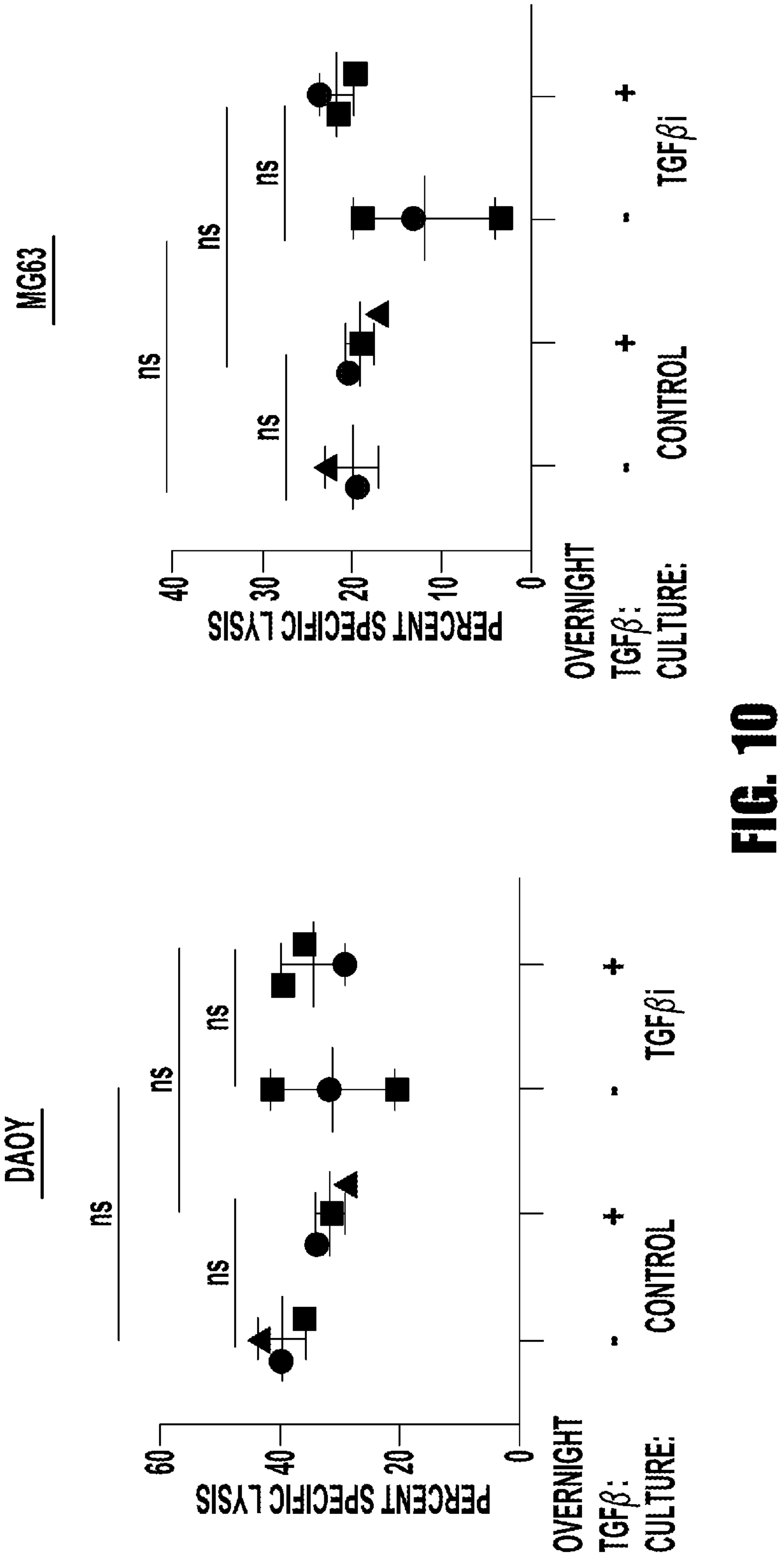

FIG. 10 provides graphs showing that TGFβi NK cells expanded with parental K562 have similar cytotoxicity to control NK cells. Control and TGFβi NK cell cytotoxicity was measured using a 4-hour calcein-release cytotoxicity assay, following overnight treatment in IL-2 alone or IL-2 and TGFβ. Individual data points (●, ■, ▲) indicate individual treatments. Lines and bars represent Mean±SD. Statistical differences were determined by two-way repeated measures ANOVA with Holm-Sidak's multiple comparisons test. * p≤0.05,  p≤0.01, * p≤0.001, **** p≤0.0001.

Figure 11:
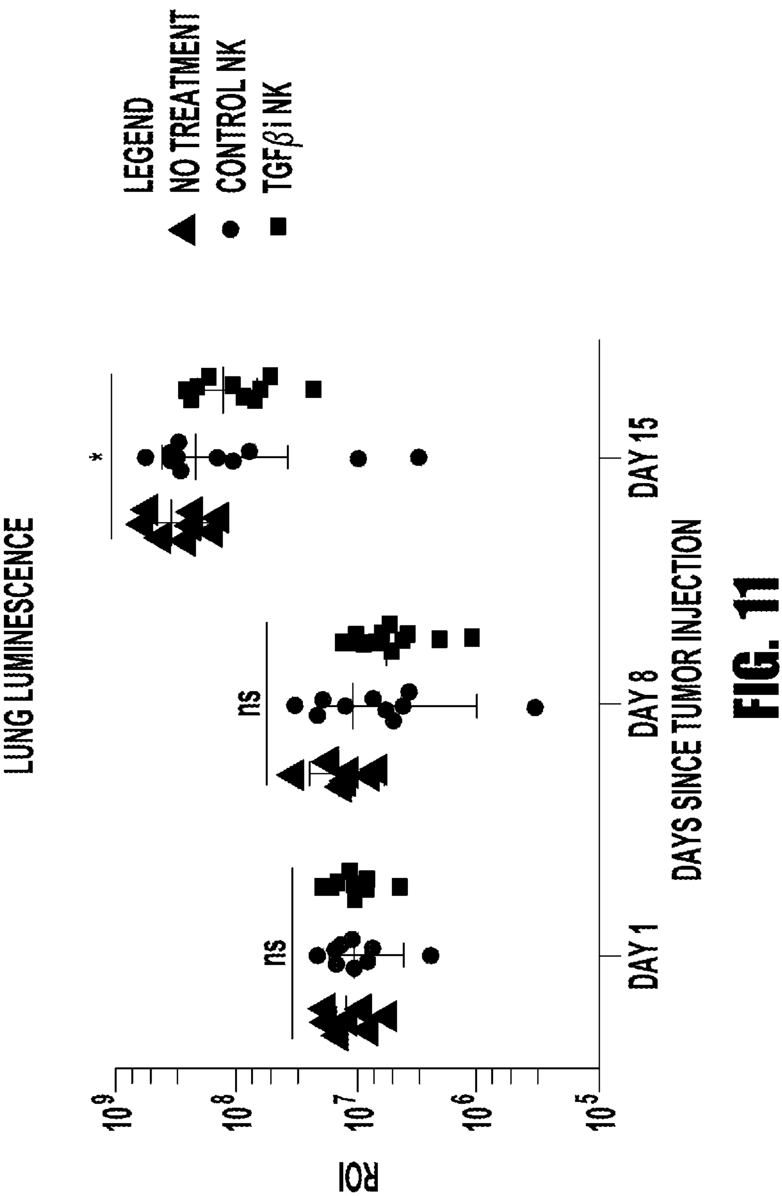

FIG. 11 provides a graph showing that expanded TGFβi NK cells control tumor growth better than control expanded NK cells in a mouse model of osteosarcoma, Treatment of mice with TGFβi NK cells expanded on K562mbIL-21 feeder cells, but not control NK cells, significantly reduces the growth of 143b osteosarcoma cell line in the lungs of NSG mice.

Figure 12A:
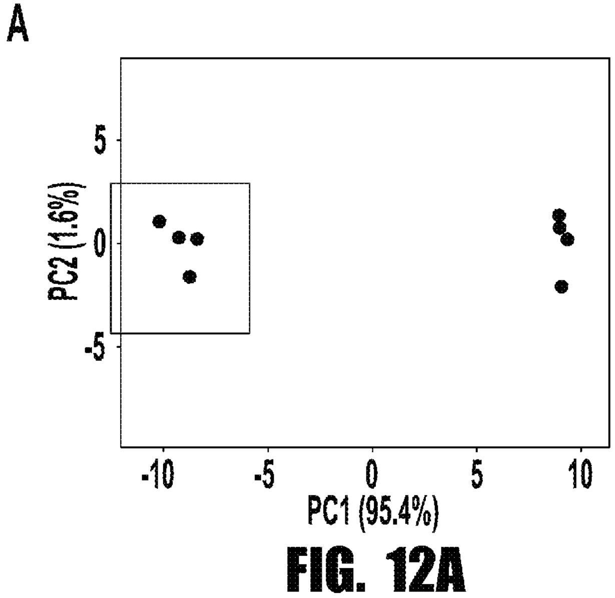
Figure 12B:
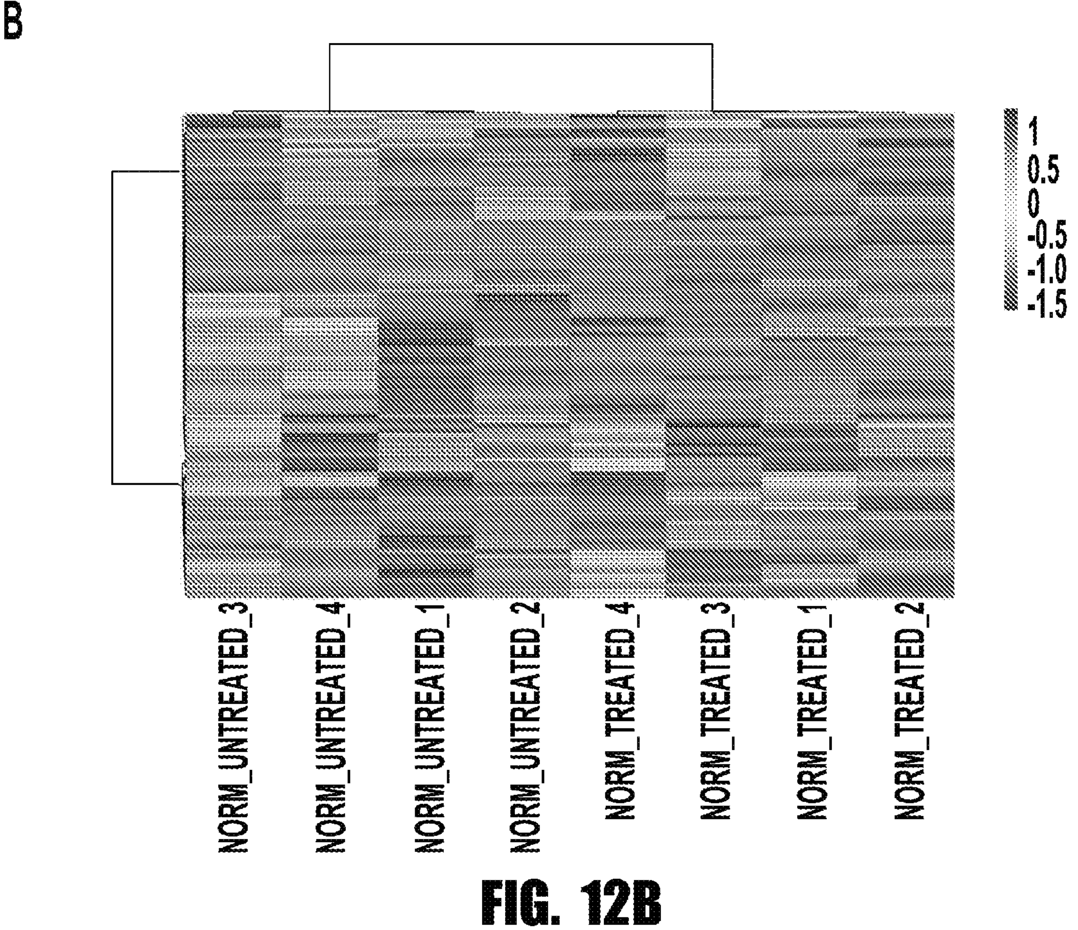

FIG. 12 provides graphs showing that TGFβi NK cells have a gene expression profile that distinguishes them from standard expanded NK cells. Standard and TGFβi NK cells were expanded in pairs on CSTX002 from 4 donors. mRNA was isolated and subjected to RNA sequencing. The top 100 differentially-expressed genes were identified. A) Principle components analysis was performed in which original values are ln(x+1)-transformed. Unit variance scaling is applied to rows; SVD with imputation is used to calculate principal components. X and Y axis show principal component 1 and principal component 2 that explain 95.4% and 1.6% of the total variance, respectively. TGFβi NK cells are identified in the red box. >95% of the variance is due to TGFβ-imprinting, whereas <2% is a result of donor variation. B) Clustering analysis was performed on the same log-transformed data. Rows are centered; unit variance scaling is applied to rows, Both rows and columns are clustered using correlation distance and average linkage.

DETAILED DESCRIPTION

The present invention provides TGF-β Imprinted Natural Killer (TGFβi NK) cells, which are highly cytotoxic, produce high levels of cytokine, and are resistant to the TGF-β Superfamily of immunosuppressive cytokines. These cells can be prepared by chronic in vitro activation of natural killer cells in the presence of a TGF-β Superfamily cytokine. The invention also provides a method of treating cancer or infection in a subject in need thereof by administering a therapeutically effective number of TGFβi NK cells to the subject.

Definitions

For clarification in understanding and ease in reference a list of terms used throughout the brief description section and the remainder of the application has been compiled here. Some of the terms are well known throughout the field and are defined here for clarity, while some of the terms are unique to this application and therefore have to be defined for proper understanding of the application.

"A" or "an" means herein one or more than one; at least one. Where the plural form is used herein, it generally includes the singular.

Also herein, the recitations of numerical ranges by endpoints include all numbers subsumed within that range (e.g., 1 to 5 includes 1, 1.5, 2, 2.75, 3, 3.80, 4, 5, etc.).

As used herein, the term "subject" can refer to any warm-blooded organism including, but not limited to, human beings, rats, mice, dogs, goats, sheep, horses, monkeys, apes, pigs, rabbits, cattle, etc. When the term is used in the context of a subject needing or requiring compositions of the present application, the term may be referred to as "a subject in need thereof" and include subjects that have been clinically diagnosed (e.g., by a medical professional, e.g., a physician) as being in need of compositions of the present application, subjects that are suspected of being in need of compositions of the present application, subjects at risk for a disease or condition and who may benefit from compositions of the present application, and subjects that are already suffering from a disease or condition and who may benefit from compositions of the present application.

The term "pharmaceutically acceptable," as used herein, refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "therapeutically effective" is intended to qualify the number or amount of an agent which will achieve the goal of decreasing disease severity while avoiding adverse side effects such as those typically associated with alternative therapies. A therapeutically effective amount may be administered in one or more doses. Treatments that are therapeutically effective include treatments that improve a subject's quality of life even if they do not improve the disease outcome per se.

An "Effective amount" generally means an amount which provides the desired local or systemic effect, e.g., effective to stimulate cytokine formation, including achieving the specific desired effects described in this application. For example, an effective amount is an amount sufficient to effectuate a beneficial or desired clinical result.

"Treat," "treating," or "treatment" are used broadly in relation to the invention and each such term encompasses, among others, preventing, ameliorating, inhibiting, or curing a deficiency, dysfunction, disease, or other deleterious process, including those that interfere with and/or result from a therapy. In various embodiments, the symptoms of a disease or disorder are alleviated by at least 5%, at least 10%, at least 20%, at least 30%, at least 40%, or at least 50%.

As used herein, the term "administer" refers to the placement of a composition (e.g., a cell composition) into a subject by a method or route which results in at least partial localization of the composition at a desired site such that desired effect is produced. A resistant natural killer cell or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

As used herein, the term "cytokine" refers to a small protein (~5-20 kDa) that is important in cell signaling, and in particular immunomodulation. Examples of cytokines include chemokines, interferons, interleukins, lymphokines, and tumour necrosis factors.

Treatment Using TGFβi NK Cells

In one aspect, the present invention provides a method of treating cancer or infection in a subject in need thereof. The method includes administering a therapeutically effective number of TGF-β Imprinted Natural Killer (TGFβi NK) cells to the subject. As described herein, TGFβi NK cells can be more effective and persist longer in vivo compared with typical expanded natural killer cells because their resistance to cytokines of the TGF-β superfamily protects them from suppression by the immune system.

As used herein, "Natural Killer Cells" ("NK cells") refer to a type of cytotoxic lymphocyte of the immune system. NK cells provide rapid responses to virally infected cells and respond to transformed cells. Typically immune cells detect peptides from pathogens presented by Major Histocompatibility Complex (MHC) molecules on the surface of infected cells, triggering cytokine release, causing lysis or apoptosis. NK cells are unique, however, as they have the ability to recognize stressed cells regardless of whether peptides from pathogens are present on MHC molecules. They were named "natural killers" because of the initial notion that they do not require prior activation in order to kill target. NK cells are large granular lymphocytes (LGL) and are known to differentiate and mature in the bone marrow from where they then enter into the circulation.

The invention includes NK cells that are resistant to cytokines of the transforming growth factor-beta (TGF-β) superfamily, and methods of making and using such resistant NK cells. The TGF-β superfamily is a large group of structurally related cell regulatory proteins. TGF-β is a multifunctional peptide that controls proliferation, differentiation and other functions in many cell types. TGF-β-1 is a peptide of 112 amino acid residues derived by proteolytic cleavage from the C-terminal of a precursor protein. These proteins interact with a conserved family of cell surface serine/threonine-specific protein kinase receptors, and generate intracellular signals using a conserved family of proteins called SMADs. The major subfamilies of the TGF-β superfamily include the TGF-β subfamily (including the TGF-β 1 to 4 isoforms), the decapentaplegic Vg-related (DVR) related proteins (e.g., bone morphogenic protein), growth differentiation factors (e.g., GDF-1 through GDF-15), and the activin and inhibin subfamily. In some embodiments, the TGFβi NK cells are resistant to TGF-β.

The TGFβi NK cells can be used to treat cancer or infection in a subject. The TGFβi NK cells are typically administered by adoptive transfer of the cells. In some embodiments, the subject has been diagnosed as having cancer. Cancer, as defined herein, is a disease based on the development of cells that contain genetic damage resulting in the relatively unrestrained growth of the cells. The genetic damage present in a cancer cell is maintained as a heritable trait in subsequent generations of the cancer cell line. The cancer treated by the method of the invention may be any of the forms of cancer known to those skilled in the art or described herein. Cancer that manifests as both solid tumors and cancer that instead forms non-solid tumors as typically seen in leukemia can be treated. The present invention provides methods for treating a subject that is afflicted with various different types of cancers, including carcinoma, sarcoma, and lymphoma.

In some embodiments, the cancer being treated is a leukemia (e.g., acute lymphoblastic leukemia; acute myeloid leukemia; chronic myelogenous leukemia, chronic lymphocytic leukemia), a myelodysplastic syndrome, a lymphoma (e.g., B cell non-Hodgkin lymphoma, Hodgkin lymphoma, T-cell lymphoblastic lymphoma, anaplastic large cell lymphoma), a solid tumor (e.g., a breast cancer, prostate cancer, gastric cancer, colon cancer, hepatocellular carcinoma, nasopharyngeal carcinoma, neuroblastoma, high grade glioma), a sarcoma (e.g., Ewing sarcoma, rhabdomyosarcoma, non-rhabdomyosarcoma soft-tissue sarcoma, osteosarcoma). In further embodiments, the cancer is selected from the group consisting of leukemia, lymphoma, rhabclomyosarcoma, brain cancer, and bone cancer.

The effectiveness of cancer treatment may be measured by evaluating a reduction in tumor load or decrease in tumor growth in a subject in response to the administration of the TGFβi NK cells. The reduction in tumor load may be represent a direct decrease in mass, or it may be measured in terms of tumor growth delay, which is calculated by subtracting the average time for control tumors to grow over to a certain volume from the time required for treated tumors to grow to the same volume.

In other embodiments, the subject being treated has an infectious disease. The TGFβi NK cells have broad-band systemic effects and can be used to treat infection by a variety of different microorganisms. As used herein, the term "infectious diseases" is means to include all diseases which are caused by infection with viruses, pathogenic bacteria, or fungi, and can be infected through respiratory organ, blood or skin contact. Non-limiting examples of such infectious diseases include, but are not limited to, hepatitis B, hepatitis C, human papilloma virus (HPV) infection, human immunodeficiency disease (HIV), cytomegalovirus infection, viral respiratory disease, influenza and so on.

TGF-β Imprinted Natural Killer Cells

Another aspect of the invention provides a natural killer (NK) cell or NK cell line cultured in the presence of a TGF-β superfamily cytokine, referred to herein as TGFβi NK cells. This includes NK cells or a cell line produced by the methods described herein, and compositions comprising the NK cells provided herein. In a particular aspect, the composition is a pharmaceutical composition comprising one or more of the NK cells or cell lines provided herein. In some embodiments, the TGFβi NK cells exhibit increased resistance to TGF-β.

The TGFβi NK cells can be allogenic or autologous cells. In some aspects, the NK cell is a mammalian NK cell. Examples of "mammalian" or "mammals" include primates (e.g., human), canines, felines, rodents, porcine, ruminants, and the like. Specific examples include humans, dogs, cats, horses, cows, sheep, goats, rabbits, guinea pigs, rats and mice. In a particular embodiment, the mammalian NK cell is a human NK cell.

The TGFβi NK cells exhibit a number of characteristics that distinguish them from naturally occurring NK cells. In some embodiments, the NK cell or cell lines exhibit increased resistance to TGF-β. In other embodiments, the NK cells produce and increased amount of interferon-γ (IFN-γ), and/or tumor necrosis factor-α (TNF-α), and/or Granulocyte-macrophage colony-stimulating factor (GM-CSF). In further embodiments, the NK cells show decreased levels of SMAD family member 3 (SMAD3) protein and/or Transforming growth factor beta receptor III (TGFBR3) protein. SMAD proteins received their name as a contraction of of the names of the *C. elegans* Sma and *Drosophila* Mad (Derynck et al., Cell, 95(6), p 737-740, 1998) and are transcriptional activators of TGF-β responses.

The TGFβi NK cells exhibit a number of characteristics that distinguish them from naturally occurring NK cells. In sortie embodiments, the NK cells have a gene expression profile substantially similar to that shown in FIG. 12. A gene expression profile that is substantially similar is one in which the gene expression is within 10% of that shown. In some embodiments, the TGFβi NK cells produce increased amounts of one or more of IFN-γ, TNF-α and GM-CSF protein. In some embodiments, the NK cell or cell lines exhibit increased expression of SCUBE1, MYO7A, KLF3, WIPF3, and EPHA1.

The TGFβi NK cells exhibit a number of characteristics that distinguish them from naturally occurring NK cells. In some embodiments, the TGFβi NK cells show decreased levels of SMAD3 protein and/or TGFBR3 protein. In some embodiments, the NK cell or cell lines exhibit decreased expression of CD300A, SGSM1, SMAD3, TBX21, and GZMK, TGFBR3, and GZMA.

Making a TGF-β-Superfamily Imprinted Natural Killer (TGFβi NK) Cell Line

Another aspect of the invention provides a method of making a TGF-β-Superfamily Imprinted Natural Killer (TGFβi NK) cell line, comprising the in vitro activation of natural killer cells in the presence of a TGF-β-superfamily cytokine. The methods can further comprise isolating or separating the one or more TGFβi NK cells produced by the methods provided herein. In addition, the methods can further comprise culturing the one or more TGFβi NK cells. In some embodiments, a TGFβi NK cell line is produced. In some embodiments, the TGFβi NK cell line is expanded in the presence of TGF-β. A cell line is a plurality of cells that can be maintained in cell culture.

Expansion (i.e., activation) refers to the ex vivo proliferation of NK cells so that the population of NK cells is increased. NK cells can be expanded, for example, from peripheral blood mononuclear cells. However, NK cells can also be expanded from other types of cells, such as hematopoietic stem cells or progenitor cells. The initial blood or stem cells can be isolated from a variety of different sources, such placenta, umbilical cord blood, placental blood, peripheral blood, spleen or liver. Expansion occurs in a cell culture medium. Suitable cell culture mediums are known to those skilled in the art, and include Basal Medium Eagle (BME), Dulbecco's Modified Eagle's Medium (DMEM), Glasgow Minimum Essential Medium (GMEM), Dulbecco's Modified Eagle's MediumiNutrient Mixture F-12 Ham (DMEM/F-12), Minimum Essential Medium (MEM), Iscove's Modified Dulbecco's Medium (IMDM), Nutrient Mixture F-10 Ham (Ham's F-10), Nutrient Mixture F-12 Ham (Ham's F-12), RPMI-1640 Medium, Williams' Medium E, STEMSPAN® (Cat. No. Stem Cell Technologies, Vancouver, Canada), Glycostem Basal Growth Medium (GBGM®), AIM-V® medium (Invitrogen), X-VIVO™ 10 (Lonza), X-VIVO™ 15 (Lonza), OPTMIZER (Invitrogen), STEMSPAN® H3000 (STEMCELL Technologies), CELLGRO COMPLETE™ (Mediatech), or any modified variants or combinations thereof.

As used herein, the term "feeder cells" refers to cells which do not have the ability to divide and proliferate, but have metabolic activity, and thus produce various metabolic products assisting in the proliferation of target NK cells. Examples of feeder cells that may be used in the present invention include, but are not limited to, animal cell lines introduced with genes, peripheral blood leukocytes (PBL) treated with various cytokines or compounds, autologous or allogeneic peripheral blood leukocytes (PBL), T-cells, B-cells, monocytes and the like. In some embodiments, the feeder cells are K562 feeder cells. In further embodiments, the K562 feeder cells are selected from clone 4 cells, clone 9 cells, and CSTX002 cells.

In some embodiments, the iii vitro activation of natural killer cells is carried out in the presence of an NK-stimulating exosome or NK-stimulating nanoparticle. Exosomes are small extracellular vesicles derived from endosomes, with a diameter between 30-100 nm. Tumor-derived exosomes carry many molecules and factors from tumor cells, and can be used to stimulate natural killer cells. See Li et al., Exp Cell Res., 363(2):141-150 (2018). Nanoparticles can also be used to stimulate natural killer cells. Nanoparticles are particles between 1 and 2500 nm in size with a surrounding interfacial layer. This includes ultrafine nanoparticles having a size from 1 to 100 nm, and fine nanoparticles having a size from 100 to 2500 nm. Nanoparticles can be prepared using a polymer, or minerals such as graphene oxide. In some embodiments, the nanoparticles are functionalized to include additional groups such as antibodies that help to stimulate natural killer cells. See, for example, Loftus et al., Nano Lett., 18(5):3282-3289 (2018).

Dosage and Administration

The TGFβi NK cells should be administered and dosed in accordance with good medical practice, taking into account the site and method of administration, scheduling of administration, patient age, sex, body weight, the nature and severity of the disorder to be treated or prevented, and other factors known to medical practitioners. The cells may be administered in a single dose or in divided doses. The pharmaceutically "effective amount" for purposes herein is thus determined by such considerations as are known in the art. The amount must be effective to achieve improvement, including but not limited to improved survival rate or more rapid recovery, or improvement or elimination of symptoms and other indicators as are selected as appropriate measures by those skilled in the art.

Typically said dose is about $10\times10^6$ cells/kg of subject weight or lower, is about $9\times10^6$ cells/kg or lower, is about $8\times10^6$ cells/kg or lower, is about $7\times10^6$ cells/kg or lower, is about $6\times10^6$ cells/kg or lower, is about $5\times10^6$ cells/kg or lower. In an alternative embodiment said dose may be between about $0.25\times10^6$ cells/kg to about $5\times10^6$ cells/kg; or more preferably about $1\times10^6$ cells/kg to about $5\times10^6$ cells/kg. Accordingly in further alternative embodiments the dose may be about $0.25\times10^6$ cells/kg, $0.5\times10^6$ cells/kg, $0.6\times10^6$ cells/kg, $0.7\times10^6$ cells/kg; $0.8\times10^6$ cells/kg; $0.9\times10^6$ cells/kg; $1.1\times10^6$ cells/kg; $1.2\times10^6$ cells/kg; $1.3\times10^6$ cells/kg; $1.4\times10^6$ cells/kg; $1.5\times10^6$ cells/kg; $1.6\times10^6$ cells/kg; $1.7\times10^6$ cells/kg; $1.8\times10^6$ cells/kg; $1.9\times10^6$ cells/kg or $2\times10^6$ cells/kg. The dose may, in other embodiments, be between 0.1 and 1 million cells/kg; or between 1 and 2 million cells/kg; or between 2 and 3 million cells/kg; or between 3 and 4 million cells/kg; or between 4 and 5 million cells/kg; or between 5 and 6 million cells/kg; or between 6 and 7 million cells/kg; or between 7 and 8 million cells/kg; or between 8 and 9 million cells/kg; or between 9 and 10 million cells/kg.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

TGFβi NK cells can be supplied in the form of a pharmaceutical composition, comprising an isotonic excipient prepared under sufficiently sterile conditions for human administration. The composition can be sterile. The formulation should suit the mode of administration. For general principles in medicinal formulation, the reader is referred to Cell Therapy: Stein Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition comprising a population of TGFβi NK cells will be adapted in accordance with the route and device used for administration.

In some embodiments, the TGFβi NK cells are administered together with a pharmaceutically acceptable carrier. Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylase or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The following example is included to demonstrate preferred embodiments of the invention. It should be appreciated by those of skill in the art that the techniques disclosed in the example, which follow represent techniques discovered by the inventor to function well in the practice of the invention, and thus can be considered to constitute preferred modes for its practice. However, those of skill in the art should, in light of the present disclosure, appreciate that many changes can be male in the specific embodiments which are disclosed and still obtain a like or similar result without departing from the spirit and scope of the invention.

EXAMPLE

Example 1: Imprinting of NK Cells by TGF-β to be TGF-β Resistant

The inventors generated human NK cells expanded with TGF-β culture (TGFβi NK) which have reduced sensitivity to TGF-β, most likely through loss of one of the key TGF-β signaling proteins-SMAD3. The inventors demonstrate: a) TGFβi NK cells have remarkably increased IFN-γ, TNF-α, and GM-CSF secretion against tumor targets and that b) TGFβi NK cells retain cytokine hypersecretion for at least 1 month post-activation.

Methods

Cell Culture:

NK cells were cultured in RPMI 1640 media supplemented with Glutamax, 10% FBS, and antibiotics. All cells were routinely tested for *Mycoplasma* contamination using Lonza MycoAlert (Lonza, LT027-58) and found to be negative at all time points. K562 feeder cells were purchased from ATCC (CCL-243) and irradiated at 100 Gy.

NK Cell Expansion:

Purified primary human NK Cells were stimulated at Day 0 1:2 with irradiated K562 and 1:1 at Day 7. The K562 cell lines used are indicated in the figure legends, as unmodified (parental), expressing 4-1BBL and membrane-bound IL-15 (Clone 4), or expressing 4-1BBL and membrane-bound IL-21 (Clone 9 or CSTX002). Standard expanded NK cells were supplemented with 50 IU/mL recombinant human IL-2, and Resistant (TGFβi NK) expanded NK cells received 50 IU/mL IL-2 and 10 ng/mL TGF-β(Biolegend, 580706). Fresh media and cytokines were added every 2-3 days. NK Cell Expansion was calculated based on the percentage of $CD3^-/CD56^+$ cells.

Flow Cytometry:

Intracellular flow cytometry was done using the BD Cytofix/Cytoperm Fixation/Permeabilization Kit with GolgiStop (BD Biosciences, 554715). Antibodies for the following proteins were used to assess NK phenotype and function: CD3 PeCy7/APC-H7, CD56 FITC/BV421, NKG2D Pe-CF594/BV510, TRAIL PE/APC/BV421, FasL PE, NKp30 PE/Alexa Fluor 647/PE-Vio615, Granzyme A APC, Granzyme B BV510, Perforin BV421, DNAM-1 BV711, CD107a BV510, IFN-γ APC, TNF-α BV421, CD16 PE, and Tonbo Ghost Dye 510/780. Cell events were acquired on a LSR Fortessa, Flow cytometry gating was determined using cells stained with viability dye only and single color controls were analyzed using FlowJo 7.6.5/10.

SMAD3 flow

Cytotoxicity Assay:

NK cells were prepared for cytotoxicity assays by resting overnight in either human IL-2 alone or IL-2 (50 IU/mL) with 10 ng/mL soluble TGF-β (Biolegend). Cytotoxicity assays with calcein-AM based method were conducted in at least duplicate using 3 μg calcein AM/mL/1,000,000 target cells in complete media. Calcein assays were conducted in the same cytokines as the NK cells were rested in overnight. Somachi et al., Journal of visualized experiments: JoVE 48, 2540 (2011).

Intracellular Function Flow Cytometry:

To determine degranulation by CD107a expression and intracellular cytokine production in response to tumors, 300,000 NK cells were co-cultured in a 96-well round-bottom plate with 60,000 tumor cells (5:1 E:T ratio) or no target for a control in 200 μl media as described for cytotoxicity assays. One μl of monensin was added to each sample along with CD107a at the beginning of the assay. Plates were spun down at 100 g×2 minutes to promote cell-cell contact, and placed in a 37° C. incubator for 3 hours. After 3 hours, media was removed and staining began for cell surface and intracellular proteins as detailed.

Cytometric Bead Array (CBA):

To determine the NK cell release of IFNγ and TNFα, NK cells were cultured as described for intracellular functional flow cytometry with the exception of the monensin and CD107a antibody. After 3 h co-culture with tumor targets or 4 h stimulation with 10 μg/mL PHA, supernatants were collected and frozen at −75° C. until use. On the day of the assay, the supernatants were thawed and 50 μl, of undiluted supernatant was used according to the manufacturer's instructions for the BD CBA Soluble Protein Master Kit (BD Biosciences, Cat#: 558265) and IFNγ and TNFα Flex Set (BD Biosciences, Cat: 558269, 560112) or MACSPlex Cytokine 12 Kit (Miltenyi, Cat: 130-099-169). The analytes were acquired on a BD LSR II or a MACSQuant. The geometric mean for each analyte was determined in Flow Jo v. 10.1 and unknown samples were interpolated using a standard curve with $R^2 \geq 0.9$ from the known standards for BD LSR II acquired samples. Analysis of MACSQuant acquired analytes was done using MACSQuantify software (version 2.8, Bergisch Gladbach, Germany). This software uses average APC median values of MACSPlex Standards and calculates the cytokine concentration in each sample.

NK Cell Activation with Cytokines:

For NK cell stimulation with IL-12, IL-15, and IL-18, primary NK cells were stimulated overnight With 10 ng/mL IL-12 (Biolegend, 573002), 50 ng/mL IL-15 (Biolegend, 570302) and 50 ng/mL IL-18 (Biolegend, 592102) as described and rested in 1 ng/mL IL-15 for 7-14 days following overnight stimulation with IL-12, IL-15, and IL-18. For determining the effect of IL-2 and TGFβ on cytokine production, the NK cells were treated as described but with the addition of IL-2 and/or TGF-β as indicated in the overnight stimulation with IL-12, IL-15, and IL-18, and along with 1 ng/mL IL-15 for 7-14 days. To measure the cytokine production, the NK cells were rested in 1 ng/mL IL-15 only overnight and throughout the assay and co-cultured with MG63 at a 5:1 ratio or equal numbers of NK cells only as a no target control and intracellular flow staining was conducted as described below."

RT-PCR/qPCR:

RNA from fresh, never frozen, Day 14 expanded human NK cells was isolated using RNAeasy Kit, QiaShredder Columns, and RNAase-Free DNase Set (all Qiagen, 74104, 79654, 79254), and cDNA was synthesized High Capacity cDNA Reverse Transcription Kit (Thermo Fisher, 4368814). PCR for the TGF-β pathway was done using Taqman Fast PCR Mastermix and Human Fast 96-well TGF-β Pathway Array (ThermoFisher, 4418742) on an Applied Biosystems 79001-IT.

Statistical Analysis:

Statistical analyses were performed as described in each figure legend using GraphPad Prism 6.0 or 7.0 (La Jolla, CA, USA). p Values less than 0.05 were considered significant.

Results and Discussion

IFNγ and TNFα are two pro-inflammatory cytokines important in the anti-tumor response and their production has been reported to be inhibited by TGF-β. To determine the production of pro-inflammatory cytokines by NK cells, NK cells were cultured for 2 weeks with parental (unmodified K562) plus or minus TGFβ. At the end of 2 weeks, control and TGFβi NK cells were incubated with tumor targets as described and supernatants were collected to measure IFN-γ and TNF-α secretion with Cytometric Bead Array. A significant increase in IFN-γ and TNFα secretion in both the presence and absence of TGF-β compared to control expanded NK cells was observed (FIG. 1).

Next, we determined whether stimulation by K562 or other tumor cells is necessary for TGFβi cytokine hyperproduction. To this end, we used IL-12, IL-15, and IL-18 which are well-established to activate NK cells in the absence of tumor stimulation. When TGFβ was added to the culture, the NK cells produced increased IFNγ and TNFα in response to tumor stimuli (FIG. 2).

To determine if other K562 feeder cells could generate TGFβi NK cells with heightened cytokine production. K562 expressing mbIL-15 (FIG. 3) or mbIL-21 (FIG. 4) were co-cultured with NK cells for 2 weeks plus or minus TGFβ. Both feeder cells induced TGFβi NK cells with increased cytokine production.

Since TGFβ has been reported to inhibit NK cell proliferation, we measured 2 week proliferation in response to K562mbIL-21 stimulation. To this end, TGFβ did not significantly affect proliferation (FIG. 5).

Next, the persistence of TGFβi NK cell phenotype and function was determined. TGFβi NK and donor-matched Standard NK cells were rested in low-dose IL-2 alone (e.g. TGFβi NK were removed from TGF-β) after completion of 2 weeks of activation. TGFβi NK cells were assessed for secretion of IFN-γ and TNF-α at the end of expansion and 7-33 days days post-activation. After activation, TGFβi NK cells maintained their increase in IFN-γ and TNF-α secretion at both baseline and with TGF-β treatment (FIG. 6).

In addition, we wanted to determine if TGFβi NK cells maintained cytokine hyperproduction in response to various stimuli. To this end, we found that TGFβi NK celsl produced increased IFNγ and TNFα in response to medulloblastoma and neuroblastoma cell lines and that this heightened production of cytokines could be induced with PHA stimulation suggesting an innate ability to produce increased anti-tumor cytokines (FIGS. 7 & 9).

The function of SMAD3 as a suppressor of NK cell anti-tumor function has been clear. SMAD3 binds directly to the IFNγ promoter to inhibit IFNγ expression and SMAD3$^{-/-}$ mice have enhanced NK cell function and decreased tumor growth. Thus, the inventors determined if SMAD3 was decreased at the protein level by western blot, and found TGFβi NK to have significantly decreased SMAD3 protein (FIG. 8).

Further, we tested the cytotoxicity of TGFβi NK cells in vitro with parental K562 cultured NK cells and in vivo with mbIL-21 expanded NK cells. Cytotoxicity was not affected (FIG. 10). In fact, in vivo TGFβi NK cells significantly decreased the growth of osteosarcoma in the lungs of NSG mice (FIG. 11).

Additionally, using RNA-seq analysis, we found that TGFβi NK cells were transcriptionally distinct from control NK cells suggesting a broad change in cell phenotype (FIG. 12) in addition to function.

In summary, human NK cells expanded with TGF-3 culture (TGFβi NK) have reduced sensitivity to TGF-β, most likely through loss of one of the key TGF-β signaling proteins-SMAD3. TGFβi NK cells have remarkably increased IFN-γ, TNF-α, and GM-CSF secretion, Surprisingly, and in contrast to previous papers, TGF-β did not inhibit the overall 2 week proliferation of TGFβi NK cells. Bellone et al., J Immunol 155: 1066-1073 (1995). The stimulation conditions used in previous papers for inducing proliferation (IL-2 and IL-15) and the time points may be key to the differences observed in proliferation. Previous measurements on TGF-β's effect on NK cell proliferation examined short-term proliferation, and not 2 week proliferation. Viel et al., Science signaling 9: ra19 (2016). The inventors propose that chronic TGF-β stimulation with tumor activation drives activation of a specific subset of NK cells, potentially those that are SMAD3$^{neg}$ to survive. These SMAD3$^{neg}$ NK cells would be resistant to phosphorylation of SMAD3 by TGF-β in the cell culture media, allowing for increased proliferation. Oida et al., Journal of immunological method 362: 195-198 (2010).

The ability of TGFβi NK cells to produce IFN-γ and TNF-α was assessed because these cytokines can both inhibit TGF-β and conversely, TGF-β can inhibit the production of IFN-γ and TNF-α. Surprisingly, remarkably increased anti-tumor IFN-γ and TNF-α secretion in TGFβi NK cells compared to Standard NK cells both with and without TGF-β treatment was found. Previous studies have demonstrated that SMAD3 deletion increases baseline IFN-γ production, therefore, it is likely that a similar mechanism is occurring in TGFβi NK cells which do not express SMAD3. Tang et al., Nat Commun 8: 14677 (2017). TGF-β is reported to inhibit TNFα production in primary NK cells (Bellone et J Immunol 155: 1066-1073 (1995)). Unexpectedly, TGFβi NK cells had significantly increased secretion of TNF-α with or without TGF-β in the assay media compared to Standard NK cells. Regulation of TNF-α production is less well-understood, but is also known to be inhibited by TGFβ, so it was unexpected to find increased TNF-α secretion in TGFβi NK cells.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

What is claimed is:

1. A method of making transforming growth factor-beta imprinted natural killer cells (TGF-βi NK), comprising activating and expanding natural killer cells in vitro by culturing the natural killer cells for at least 14 days in the presence of one of feeder cells, exosomes, or nanoparticles that express membrane bound interleukin-21 (IL-21) or membrane bound interleukin-15 (IL-15) and in the presence of an amount of TGF-β sufficient to render the natural killer cells resistant to TGF-β, wherein the resulting natural killer cells are TGF-βi NK cells that maintain cytotoxicity relative to control NK cells cultured without the presence of TGF-β.

2. The method of claim 1, wherein the membrane bound IL-21 is expressed on K562 feeder cells.

3. The method of claim 2, wherein the K562 feeder cells are irradiated.

4. The method of claim 2, wherein an initial ratio of NK cells to K562 feeder cells is about 2:1 at Day 0 of activation and expansion.

5. The method of claim 4, wherein a second ratio of natural killer cells to K562 feeder cells is about 1:1 at Day 7 of activation and expansion.

6. The method of claim 1, wherein the natural killer cells are cultured in the presence of exosomes that express membrane bound IL 21 or nanoparticles that express membrane bound IL-21.

7. The method of claim 1, wherein the membrane bound IL-15 is expressed on K562 feeder cells.

8. The method of claim 1, wherein the amount of TGF-β is about 10 ng/mL.

9. The method of claim 1, wherein the natural killer cells are cultured in the presence of K562 feeder cells expressing 4-1BBL and membrane bound IL-15.

10. The method of claim 1, wherein the natural killer cells are cultured in the presence of K562 feeder cells expressing 4-1BBL and membrane bound IL-21.

11. The method of claim 1, wherein the TGF-βi NK cells produce increased amounts of one or more of IFN-γ, TNF-α, and GM-CSF as compared to control NK cells cultured without the presence of TGF-β.

12. The method of claim 1, wherein the TGF-βi NK cells exhibit decreased levels of SMAD3 protein and/or TGFBR3 protein as compared to control NK cells cultured without the presence of TGF-β.

13. The method of claim 1, wherein the TGF-βi NK cells exhibit increased expression of SCUBE1, MYO7A, KLF3, WIPF3, and EPHA1 and/or exhibit decreased expression of CD300A, SGSM1, SMAD3, TBX21, GZMK, TGFBR3, and GZMA as compared to control NK cells cultured without the presence of TGF-β.

14. The method of claim 1, wherein resistance of the TGFβi NK cells to TGF-β is mediated by SMAD3 down-regulation.

15. The method of claim 14, wherein resistance of the TGFβi NK cells to TGF-β persists for at least one week in vitro after TGFβi NK cells are removed from TGF-β.

* * * * *